(12) United States Patent
Watt

(10) Patent No.: US 7,936,910 B2
(45) Date of Patent: May 3, 2011

(54) METHOD, SYSTEM AND SOFTWARE FOR DISPLAYING MEDICAL IMAGES

(76) Inventor: James Hamilton Watt, Hamilton (CA)

( * ) Notice: Subject to any disclaimer, the term of this patent is extended or adjusted under 35 U.S.C. 154(b) by 882 days.

(21) Appl. No.: 11/858,455

(22) Filed: Sep. 20, 2007

(65) Prior Publication Data

US 2009/0080719 A1    Mar. 26, 2009

(51) Int. Cl.
*G06K 9/00* (2006.01)

(52) U.S. Cl. ........ 382/128; 382/129; 382/130; 382/131; 382/132; 600/425; 600/437; 600/407; 378/62; 378/98; 345/156; 345/115; 345/116; 345/117

(58) Field of Classification Search ............ 600/407, 600/425, 437; 382/128, 129, 130, 131; 128/920; 345/113, 114, 115, 116, 156, 117; 378/62, 378/98

See application file for complete search history.

(56) References Cited

U.S. PATENT DOCUMENTS

| | | | |
|---|---|---|---|
| 5,454,075 | A | 9/1995 | Kudo |
| 5,987,345 | A * | 11/1999 | Engelmann et al. .......... 600/407 |
| 6,628,243 | B1 | 9/2003 | Lyons et al. |
| 6,993,167 | B1 | 1/2006 | Skladnev et al. |
| 7,536,644 | B2 * | 5/2009 | Fowkes et al. ............... 715/720 |
| 7,630,531 | B2 * | 12/2009 | Chui ............................. 382/128 |
| 2002/0039084 | A1 | 4/2002 | Yamaguchi |
| 2003/0142119 | A1 | 7/2003 | Akagi |
| 2003/0179155 | A1 | 9/2003 | Someya |
| 2005/0285812 | A1 | 12/2005 | Shimayama et al. |
| 2006/0215895 | A1 * | 9/2006 | Ando ............................. 382/128 |
| 2006/0229748 | A1 * | 10/2006 | Yarger et al. ..................... 700/83 |
| 2007/0122021 | A1 | 5/2007 | Zingaretti et al. |
| 2007/0177780 | A1 * | 8/2007 | Chui ............................. 382/128 |
| 2008/0193000 | A1 | 8/2008 | Seghers et al. |

FOREIGN PATENT DOCUMENTS

| | | |
|---|---|---|
| JP | 2000-166878 | 6/2000 |
| JP | 2000166878 | 6/2000 |

OTHER PUBLICATIONS

Fax communication for examiner amendment print out ,from Mr. Peter Elyjiw on Dec. 10, 2010.*

* cited by examiner

*Primary Examiner* — Wesley Tucker
*Assistant Examiner* — Nancy Bitar

(57) ABSTRACT

In a system for displaying medical images, a first linear array of medical images representing multiple views of a patient taken approximately contemporaneously may be displayed. The images may automatically be ordered within the array based on the represented views. A second linear array of medical images adjacent to the first linear array may contemporaneously be displayed. The images of the second linear array may represent the same views of the patient as in the first linear array taken approximately contemporaneously but at an earlier time from the images of the first linear array. Like views of the patient may be aligned as between the first linear array and the second linear array. Correlation of features between images may thus be facilitated. Alternatively, one or more principal views and one or more non-principal views of a patient in a set of medical images may be identified. Each principal view may automatically be displayed in a particular size on a separate display of an array of displays, while each non-principal view may automatically be displayed on the remaining display or displays of the array in a smaller size.

23 Claims, 9 Drawing Sheets

128 — ▨▨▨▨ (fully hatched 2×2)

126 — 
| 15 | ▨ |
| 14 | 17 |
| 13 | 16 |
(3×2: 13,14,15 / 16,17,▨ — shown as)
| 15 | ▨ |
| 14 | 17 |
| 13 | 16 |

128 — ▨ (fully hatched 3×3)

126 — ▨ (fully hatched 3×3)

124 — 
| 12 | 15 | ▨ |
| 11 | 14 | 17 |
| 10 | 13 | 16 |

122 — 
| 3 | 6 | 9 |
| 2 | 5 | 8 |
| 1 | 4 | 7 |

I = 17

METHOD, SYSTEM AND SOFTWARE FOR DISPLAYING MEDICAL IMAGES

FIELD OF THE INVENTION

The present invention relates to medical imaging, and more particularly to a method, system and software for displaying medical images.

BACKGROUND

In laboratories which perform medical imaging such as X-ray, Magnetic Resonance Imaging (MRI), Computed Tomography (CT), Positron Emission Tomography (PET), or ultrasound imaging, multiple medical images of a patient are usually taken, substantially contemporaneously, in an imaging session. The images may be referred to collectively as a "study". A single study typically includes multiple views of the patient, such as a front view (which may be called the anterior-to-posterior, or AP view, or the posterior-to-anterior, or PA view, depending upon whether the film is behind or in front of the patient), a lateral view, and an oblique view. The number and types of views in a study may be based on the region of the body being imaged. For example, the above-noted three views are typically taken for studies involving the shoulder, hand, thumb, finger, foot, or toe; at least five views are typically taken for studies involving the lumbar spine; and at least seven views may be taken for studies involving the cervical spine.

After medical images have been captured and digitized, they are conventionally assembled into an electronic file which is transmitted over the Internet to a radiologist. Several studies may be combined or "bundled" into one electronic file, such that there may be as many as sixty or more digital images in the file.

In a known system, the radiologist is provided with one (colour) monitor for displaying text and two (black and white) monitors for displaying images. Software allows the radiologist to select a study whereupon the requisition appears on the text monitor and a thumbnail of each of the images appears on the left hand side of the first image monitor. The radiologist may select a view type, namely, a split-4 or split-9 screen, whereupon the screen of the first image monitor is divided into 4 or 9 cells and the first 4 or 9 images are displayed. The radiologist may then request display of the next 4 or 9 images, and so on. Additionally, the radiologist may drag an image from one of the cells to the second image monitor in order to obtain a full screen display of that image.

Problematically, the images of a study are in no guaranteed order. Further, the image size on a split 4 or 9 screen may be insufficient to allow the radiologist to see important details. Moreover, consecutively looking at full sized images dragged to the second screen may not allow the radiologist to proper correlate features from different views or to correlate features from the same view taken at different times, e.g. for the purpose of tracking the progression of a medical condition.

Another problem is that current approaches for recording audio (e.g. dictated notes, such as preliminary diagnoses) in conjunction with displayed medical images may not permit a recording associated with a study to be selectively controlled in the case where multiple recordings exist for a bundle of studies in an electronic file.

A solution which obviates or mitigates one or more of the above-noted problems would be desirable.

SUMMARY OF THE INVENTION

In accordance with one aspect of the present invention there is provided a computer-implemented method comprising: displaying a first linear array of medical images representing multiple views of a patient taken approximately contemporaneously, the images being automatically ordered within the array based on the represented views; and contemporaneously displaying a second linear array of medical images adjacent to the first linear array, the images of the second linear array representing the same views of the patient as in the first linear array and being taken approximately contemporaneously but at an earlier time from the images of the first linear array, such that like views of the patient are automatically aligned as between the first linear array and the second linear array.

In accordance with another aspect of the present invention there is provided a computer-implemented method comprising: identifying one or more principal views of a patient in a set of medical images; further identifying one or more non-principal views of the patient in the set of medical images; automatically displaying each principal view in a particular size on a separate display of an array of displays; and automatically displaying each non-principal view on the remaining display or displays of the array in a size that is smaller than the particular size.

In accordance with another aspect of the present invention there is provided a system for displaying medical images comprising a controller and at least one display, the controller being operable to: display on the at least one display a first linear array of medical images representing multiple views of a patient taken approximately contemporaneously, the images being automatically ordered within the array based on the represented views; and contemporaneously display on the at least one display a second linear array of medical images adjacent to the first linear array, the images of the second linear array representing the same views of the patient as in the first linear array and being taken approximately contemporaneously but at an earlier time from the images of the first linear array, such that like views of the patient are automatically aligned as between the first linear array and the second linear array.

In accordance with another aspect of the present invention there is provided a machine-readable medium storing instructions which, when executed by a controller of a medical imaging system, cause the controller to: display a first linear array of medical images representing multiple views of a patient taken approximately contemporaneously, the images being automatically ordered within the array based on the represented views; and contemporaneously display a second linear array of medical images adjacent to the first linear array, the images of the second linear array representing the same views of the patient as in the first linear array and being taken approximately contemporaneously but at an earlier time from the images of the first linear array, such that like views of the patient are automatically aligned as between the first linear array and the second linear array.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

In the figures which illustrate exemplary embodiments of this invention:

FIGS. 9A-9D are schematic representations of displayed medical images illustrating various approaches for apportioning images to displays.

DETAILED DESCRIPTION

Figure 1:
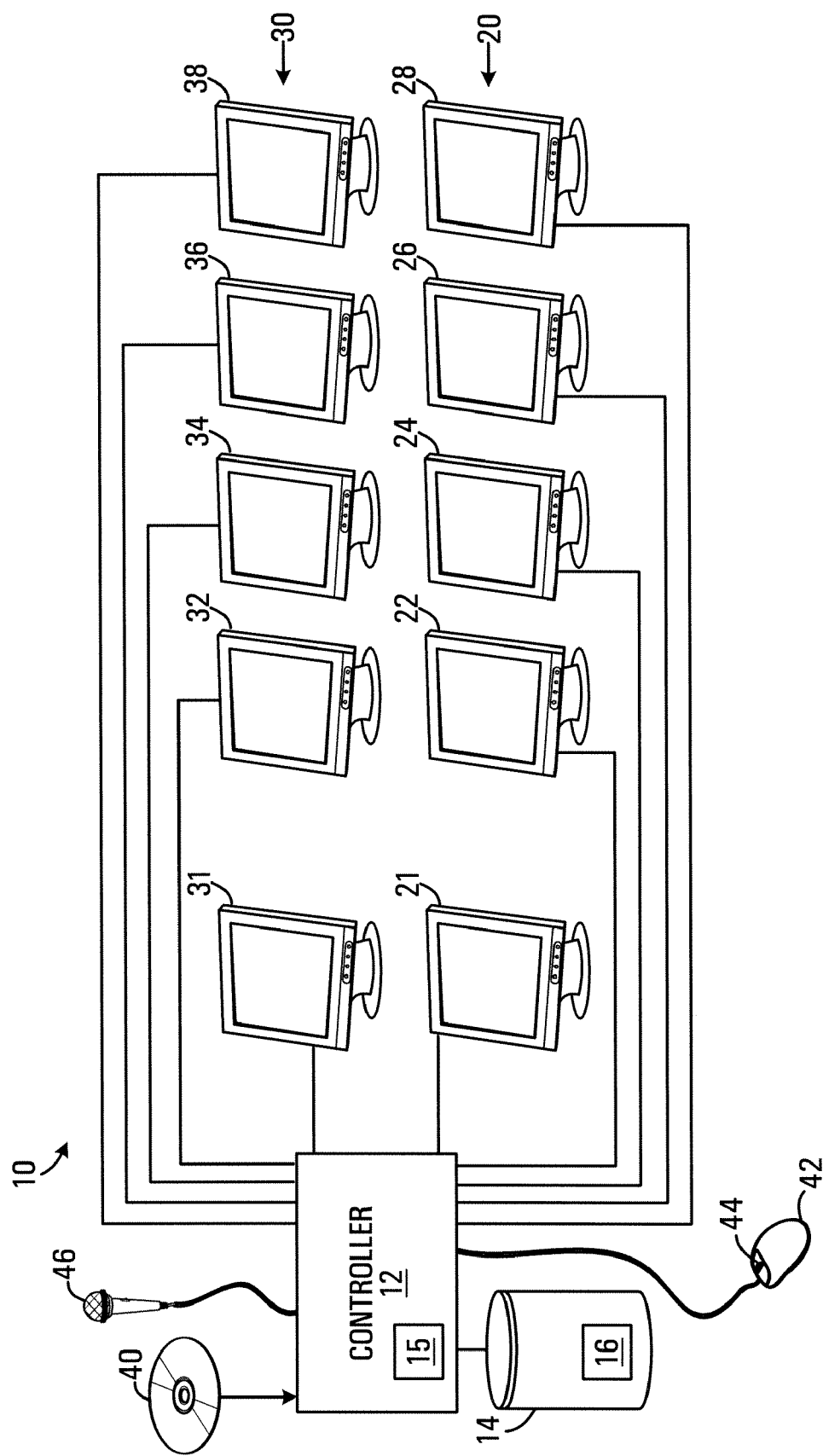
FIG. 1 is block diagram of a medical imaging system.

FIG. 1 is a block diagram illustrating an exemplary medical imaging system 10. As shown in FIG. 1, the system 10 includes a controller 12 interconnected with ten displays 21, 22, 24, 26, 28, 31, 32, 34, 36 and 38, which are collectively referred to as displays 18. The controller 12 controls the display of medical image data 16 of a patient on displays 18. The displays 18 may be Liquid Crystal Displays (LCDs), OLEDS, or the like. The displays 18 are physically arranged into two rows of displays 20 and 30 containing five displays each. Each row 20 or 30 of displays may be referred to generically as a "linear array" of displays. Rows 20 and 30 are adjacent to one another, with the first row 20 being below the second row 30 in the present embodiment. The displays 21, 22, 24, 26 and 28 of the first row 20 are horizontally aligned with the displays 31, 32, 34, 36 and 38, respectively, of the second row 30. The physical arrangement of the displays 18 may be achieved by mounting the displays to a wall for example. In this case, flat panel displays may be particularly desirable for their compactness and limited weight.

The controller 12 may be one or more conventional computers, servers or workstations, each comprising one or more processors interconnected with volatile memory and non-volatile memory 14 in a conventional manner. The controller 12 executes medical imaging software 15 which governs the manner in which the medical image data 16 is displayed on displays 18. The medical imaging software 15 may be loaded from a machine-readable medium 40 such as an optical disk or magnetic medium. The controller 12 has a user input mechanism 42, which in the present embodiment is a mouse having a scroll wheel 44 with detents to facilitate uniform scrolling. The controller also has a microphone 46. Other conventional components of the controller 12, such as a keyboard for typing commands or a network interface card for the purpose receiving medical image data 16 from a network for example, have been omitted for brevity. As will be appreciated, execution of software 15 causes medical images to be displayed on displays 18 in a manner that facilitates correlation of features from different views and/or features from the same view taken at different times.

Each row of displays 20, 30 includes a first display 21, 31 for displaying textual information and four displays 22, 24, 26, 28 and 32, 34, 36, 38 (respectively) for displaying medical images. The displays 21, 22 may be referred to as "textual displays" while the displays 22, 24, 26, 28, 32, 34, 36, 38 may be referred to as "graphical displays". The textual information may be requisitions by which the images were requested by a medical professional or technician's reports from the technician(s) who created the images responsive to receiving the requisitions. In some embodiments, the first display 21, 31 may be a lower-resolution display (sufficient for displaying text) while the remaining displays may be high resolution displays (advantageous for viewing detailed medical images). The high-resolution displays may be black and white displays, which may be sufficient when the medical images are black-and-white images. However, this is not a requirement, and in fact, medical images could be presented in color.

Medical image data 16 contains multiple medical images, such as multiple X-rays for example, representing different views of a patient. Medical image data 16 is illustrated in greater detail in FIG. 2.

Figure 2:
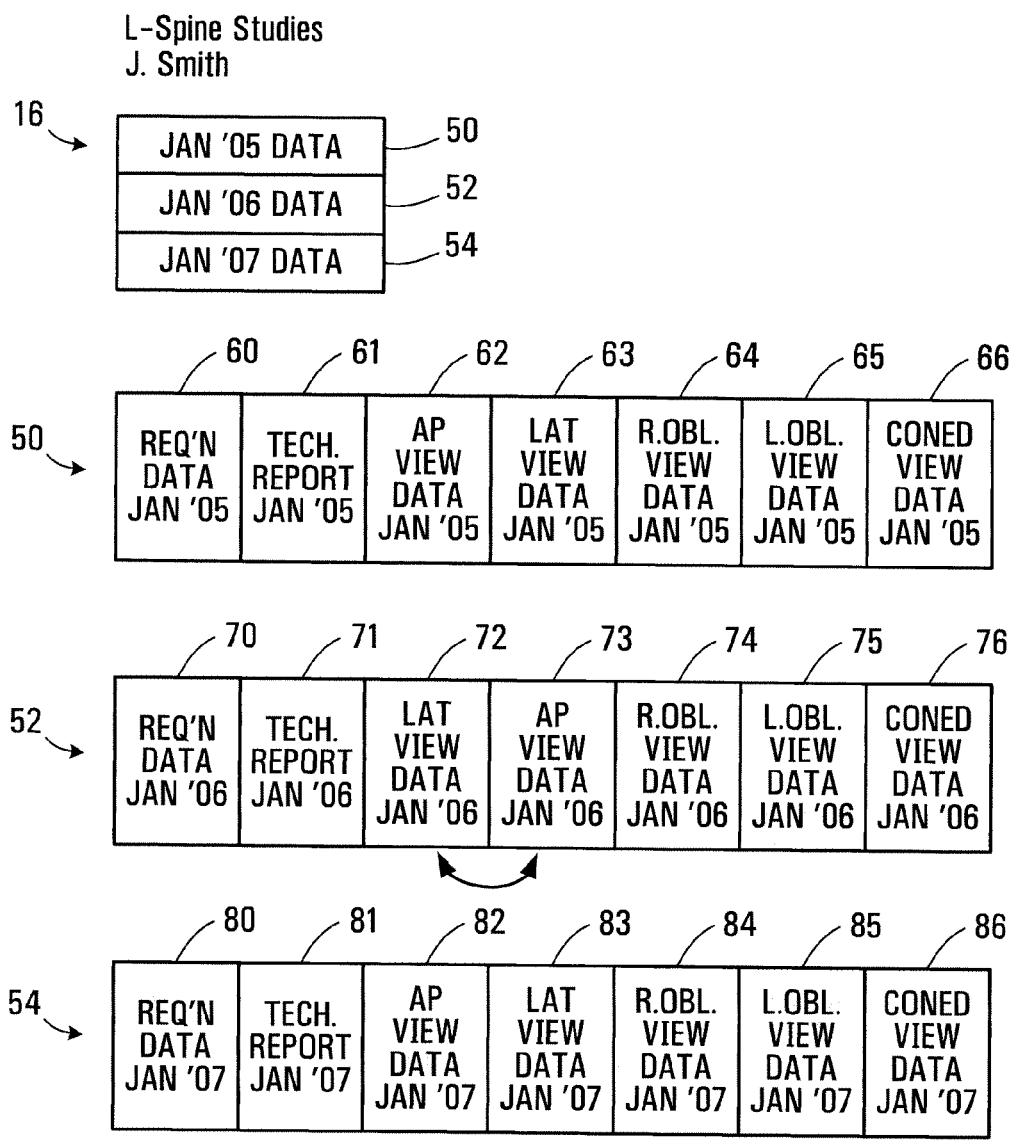
FIG. 2 is a schematic representation of exemplary medical image data to be displayed by the system of FIG. 1.

As shown in FIG. 2, exemplary medical image data 16 is one or more electronic files representing three lumbar spine studies 50, 52 and 54 for a particular patient, J. Smith. Each study was taken in a separate imaging session at a different time from the other studies. In particular, study 50 was taken in January, 2005; study 52 was taken in January, 2006; and study 54 was taken in January, 2007.

Each study contains textual data as well as medical image data. With reference to study 50, the textual data includes textual requisition data 60 and technician report data 61, whereas the medical image data includes data for five separate images representing five different views of the patient taken substantially contemporaneously in a single imaging session. In the present example, the views consist of an AP view, a lateral view, a right oblique view, a left oblique view, and a coned down view, which are considered to be standard views for lumbar spine studies. The data for the five images representing these views is shown in FIG. 2 at 62, 63, 64, 65 and 66, respectively.

The other two studies 52 and 54 are similar in composition to study 50. That is, study 52 includes textual data 70, 71 and image data 72, 73, 74, 75 and 76, and study 54 includes textual data 80, 81 and image data 82, 83, 84, 85 and 86. One distinction of study 52 is that the order of the AP view 73 and the lateral view 72 data within the study is reversed in relation to the order of the AP view and lateral view image data of the other two studies. This illustrates the fact that the order of views within a study can vary between studies, even for the same patient.

The data 16 may be automatically compiled by the controller 12 through local storage in non-volatile memory 14 of studies 50, 52 and 54 as they are received overtime, and association of the studies by patient name. Alternatively, the data 16 may be received as a unit.

Figure 3:
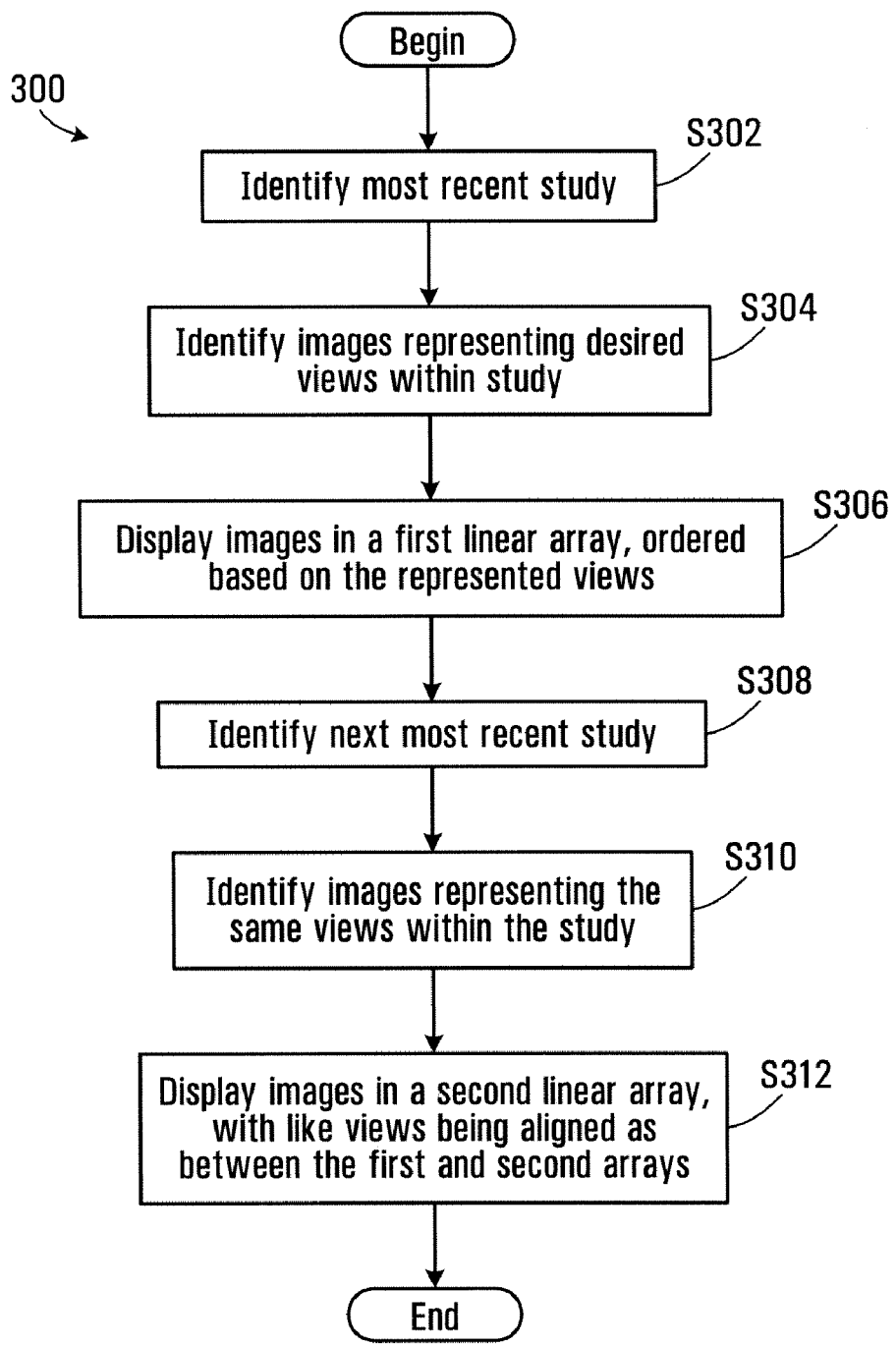
FIG. 3 is a flowchart of operation of the system of FIG. 1 for displaying medical images.
Figure 4:
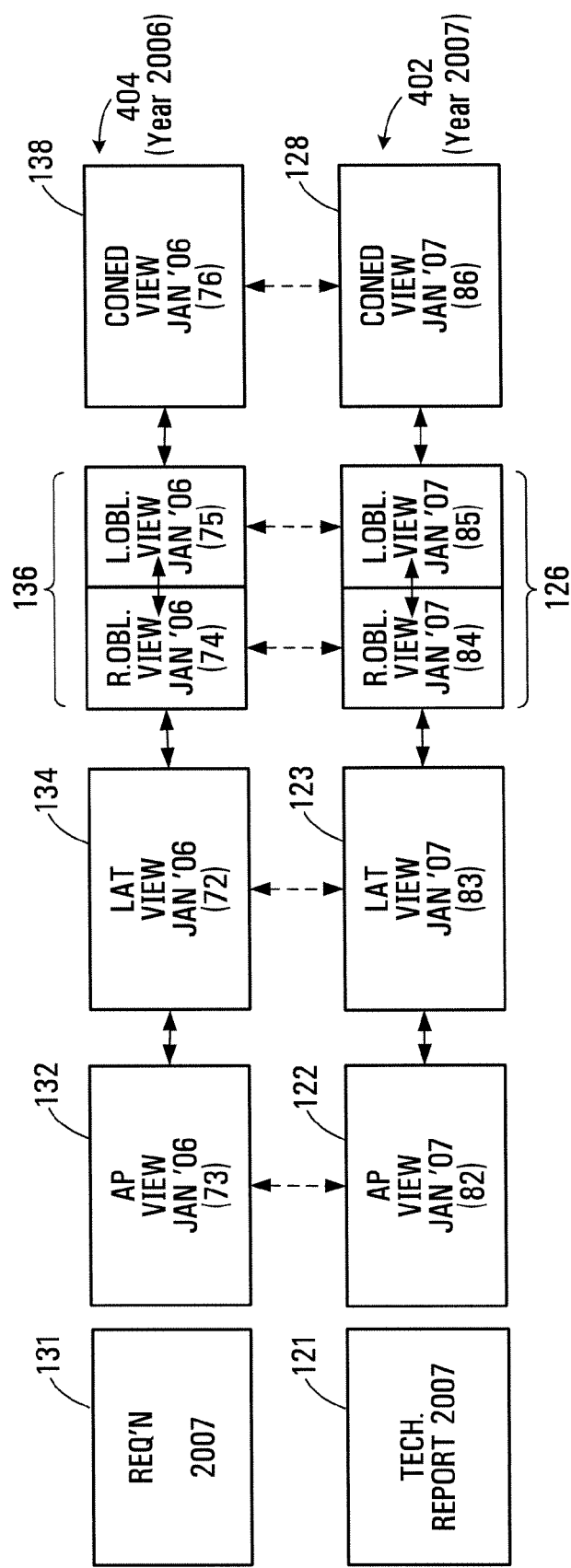
FIG. 4 is a schematic representation of the displayed medical images which result from the operation of FIG. 3.

Operation 300 of the controller 12 for displaying medical image data is illustrated in FIGS. 3 and 4. FIG. 3 illustrates a flowchart of operation 300 of the controller 12 while FIG. 4 illustrates the images displayed on displays 18 as a result of that operation. FIG. 4 adopts the convention of identifying the content of a display using a reference numeral that is the same as the reference numeral used to identify the relevant display in FIG. 1 plus 100. Thus, the content of display 21 of FIG. 1 is illustrated in FIG. 4 at 121; the content of display 22 is illustrated at 122; and so forth.

Initially, the most recent study within medical image data 16 (FIG. 2) is identified (FIG. 3, S302). The most recent study is identified first because this data is usually of the greatest interest to the user of system 10 (e.g. a radiologist), at least initially. Accordingly, study 54 of FIG. 2, which was taken in January 2007, is identified first, as the "current study". The controller 12 at this stage displays the textual requisition data 80 and technician report data 81 associated with the current study on textual displays 31 and 21, respectively. Thereafter, images representing desired views within the study are automatically identified (S304). Automatic identification of the desired views may be facilitated by suitable tagging of the images within medical image data 16 upon their generation, or could be achieved through other methods, such as pattern recognition. In the case of the lumbar spine study of the present example, the five above-noted standard views represent the desired views. Accordingly, the image data associated with these views is identified within the study at 82, 83, 84, 85 and 86.

The images represented by data 82, 83, 84, 85 and 86 are then displayed on the graphical displays 22, 24, 26 and 28 of the first row 20 (S306). This results in the display of a first linear array of medical images 402 (FIG. 4). The images are automatically ordered within the array 402 based on the represented views. In the present embodiment, the automatic ordering is predetermined based on the region being viewed (the lumbar spine). In some embodiments, the ordering can be configured by the user, e.g. on a user-specific basis. More specifically, in the case of the lumbar spine study of the present example, each of the AP, lateral and coned down views is displayed, in full screen size, on displays 22, 24 and 28 respectively, whereas the right oblique and left oblique views are both displayed on a single display 26. That is, display 26 automatically adopts a split-screen mode to present two views on a single display, since the number of present images (5) exceeds the number of graphical displays (4). The size of the images presented on display 26 is automatically adjusted, e.g. by cropping or scaling of the images, to accommodate both of the views on a single display 26. In general, each view which is considered to be a "principal view" may be presented full-screen on a separate display, while non principal view(s), if any, are presented on the remaining display(s), in reduced size (e.g. thumbnail) form. The identification of principal views and non-principal views is preprogrammed, and may be based on the region of the body being viewed. Selection of a reduced-size image by the user expands the image to full screen size; selection of the expanded image reverts it to its reduced size. This approach can be adapted even in embodiments having only one array of displays.

The resulting array of images 402 representing the current study is as shown in FIG. 4. In each image of FIG. 4, the source of the image data from the relevant study 54 is parenthetically indicated, for clarity.

Subsequently, the next most recent study 52, taken in January 2006, is automatically identified within medical image data 16 (S308). Images representing the same, desired views are identified within study 52 (S310), as was done previously for study 54 (at S304). The identified images are then displayed on graphical displays 32, 34, 36 and 38 of the second row 30 (S312) to create a second linear array of images 404 (FIG. 4). These images are displayed in the same order as the images displayed in the first row 20, such that like views of the patient are aligned as between the first linear array of images 402 and the second linear array of images 404. It should be noted that, in the present example, the automatic ordering includes ordering the January 2006 lateral and AP views in the opposite order in which the data 72, 73 for these views appears within study 52 (FIG. 2). The resulting alignment of images between the rows of displays (i.e. between the first array of images 402 representing the current study and the second array of images 404 representing the "previous study") is represented in FIG. 4 by dashed, two-headed arrows. Advantageously, this alignment of the images facilitates correlation of features from the same view of a patient taken at different times, which can be helpful in diagnosing progressive medical conditions. Moreover, this result is achieved conveniently, with little or no user input being required, by virtue through the fact that identification, ordering and display of images is performed automatically by the controller 12 executing software 15. This capability allows the viewer to begin analyzing the medical images more quickly than in known systems, in which the user must initially spend time configuring the system to display data as desired. Operation 300 is thus concluded.

It will be appreciated that the automatic display of different views of the patient adjacent to one another within each linear array, as shown in FIG. 4, may additionally facilitate correlation of features between different views of the same study taken substantially contemporaneously. This correlation between views is represented in FIG. 4 by solid, two-headed arrows. Vertical alignment of adjacent images within the linear array, as well as the choice of appropriate views to be presented adjacent to one another within the linear array, may enhance this effect.

Figure 5:
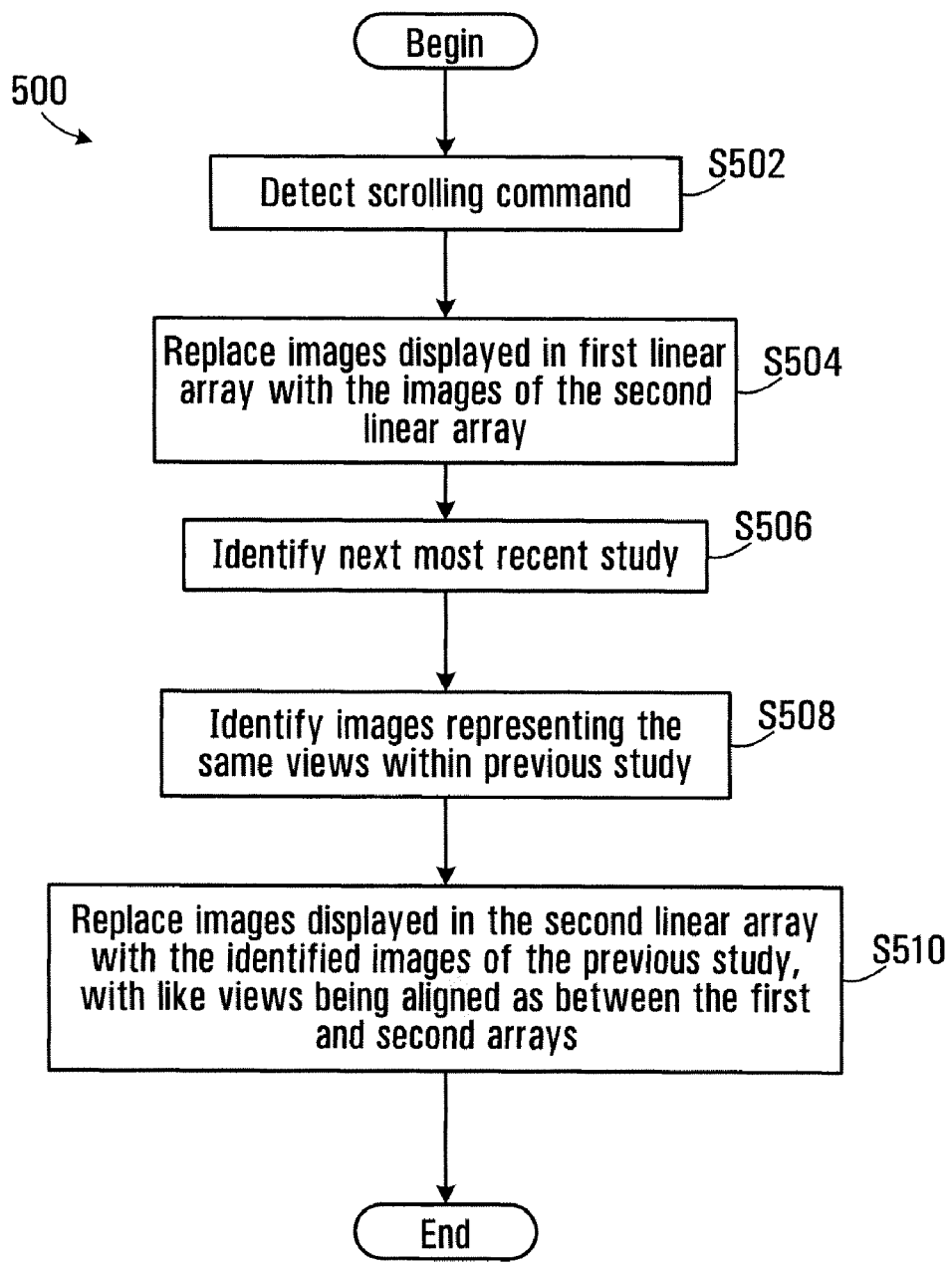
FIG. 5 is a flowchart of operation of the system of FIG. 1 for displaying historical medical image data.
Figure 6:
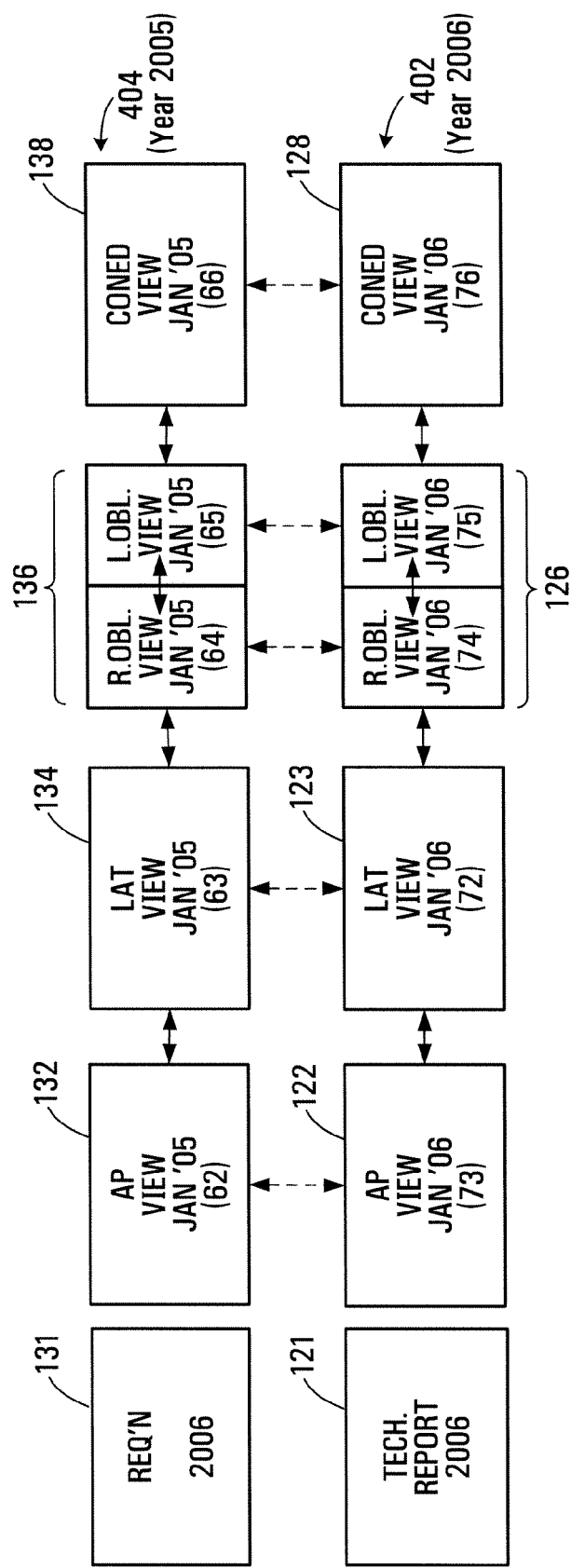
FIG. 6 is a schematic representation of the displayed medical images which result from the operation of FIG. 5.
Figure 7A:
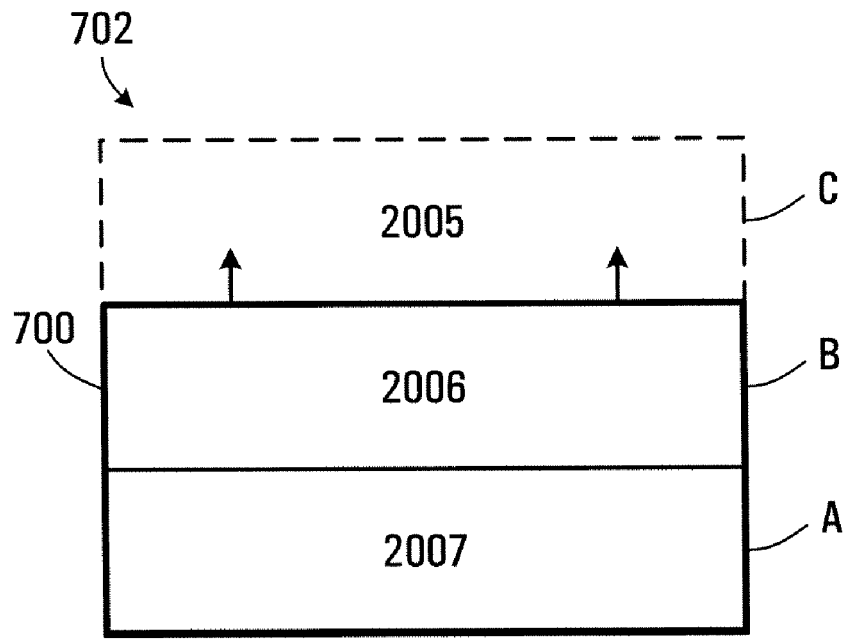
FIGS. 7A and 7B are block diagrams which conceptually illustrate the display of historical medical image data.
Figure 7B:
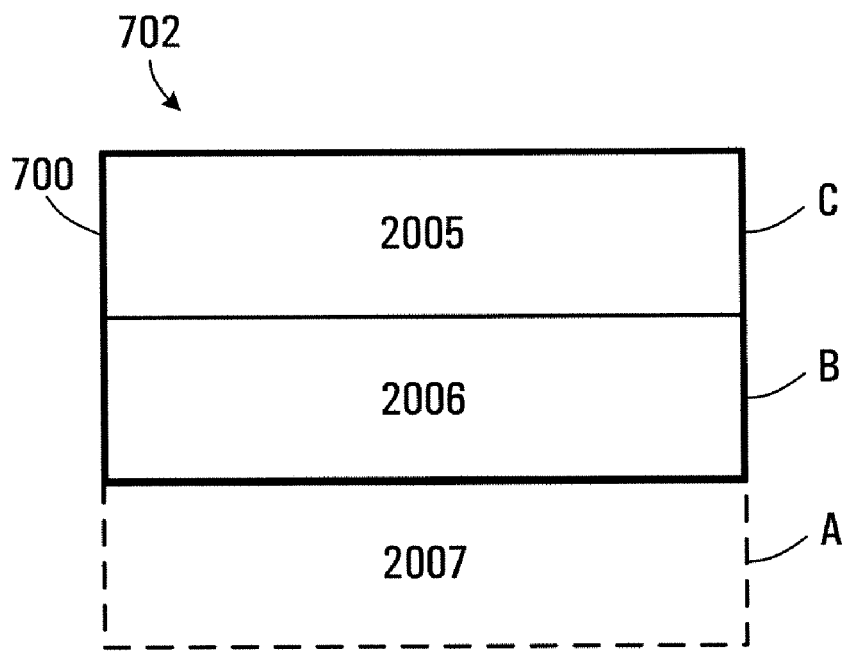

The user of system 10 who is viewing the medical images of FIG. 4 may wish to view earlier medical images from a previous study for the same patient. The user may for example need to consider the early images to assess the early stages of a progressive a medical condition. This operation is illustrated in FIGS. 5, 6, 7A and 7B. More specifically, FIG. 5 illustrates a flowchart of operation 500 of the controller 12. FIG. 6 illustrates the images displayed on displays 18 based on operation 500, using the same conventions as FIG. 4. FIGS. 7A and 7B conceptually illustrate the operation 500.

Initially, the user rotates the scroll wheel 44 of a mouse 42 from a first detent position to a second detent position. This action generates a scrolling command, indicative of the fact that the user wishes to view earlier image data.

When the controller 12 detects the scrolling command (S502), it replaces the images displayed in the first linear array of images 402 with the images of the second linear array 404 (S504). In other words, the January 2007 images which had been displayed in the first row of displays 20 (FIG. 1) are replaced with the January 2006 images of the second row of displays 30. The January 2006 study thus effectively becomes the "current study". At this stage, the controller 12 may also discontinue displaying the textual requisition data 80 and technician report data 81 of the former current study on textual displays 31 and 21, respectively, and commence displaying data 70, 71 of the new "current study" in its place.

The controller 12 then identifies the next most recent study (S506) within medical image data 16, which in the present example is the study with the latest date that is earlier than January 2006. Accordingly, study 50 (FIG. 2), dated January 2005, is identified as the next most recent study. Thereafter, images representing the same views of the patient as were displayed initially are automatically identified within the study 50 (S508). This results in the identification of image data 62, 63, 64, 65 and 66 as being representative of the desired views.

The controller 12 then replaces the images displayed in the second array 404 (i.e. the January 2006 images) with the above-identified images from study 50 (i.e. the January 2005 images). In other words, the January 2005 study effectively becomes the "previous study" instead of the January 2006 study, which is now displayed as the "current study". The January 2005 images are ordered in the same way as the previously displayed images, such that like views of the patient are again aligned as between the first linear array of images 402 and the second linear array of images 404. The resulting display images are as shown in FIG. 6. Advantageously, by entering a single scrolling command, the user has now adjusted multiple displays within system 10 to show an earlier study. Moreover, the images of that study are automatically displayed in a fashion that is consistent with the previously displayed study, providing all of the advantages noted above. Operation 500 is thus concluded.

The above described operation 500 may be thought of as sliding a conceptual viewing window 700 though a chronological bundle 702 of studies A, B, and C. This is illustrated in FIGS. 7A and 7B. The window 700 "exposes" two studies at a time and is capable of sliding, study by study, through the bundle, at the request of the user. For example, before operation 500 is performed, the position of the conceptual viewing window 700 may initially be considered to allow the user to see medical images associated with the most recent studies A and B (e.g. the January 2007 and January 2006 studies), as shown in FIG. 7A and FIG. 4. Thereafter, execution of operation 500 causes the viewing window 700 to "slide upwardly", such that the medical images that are now exposed through the window are those associated with studies B and C (e.g. the January 2006 and January 2005 studies), as shown in FIG. 7B and FIG. 6.

Although not expressly illustrated, it is also possible to scroll through the data in the opposite chronological direction (i.e. from older studies to more recent studies), by rotating the scroll wheel 44 in the opposite direction, e.g. from the second detent position back to the first detent position. It is noted that a scroll wheel with detents may be preferable to a scroll wheel without detents, since uniform, predictable scrolling (e.g. advancing one study per detent) may be promoted.

Regardless of which studies are displayed on displays 18 of system 10 at any given time, the user may wish to record dictated notes in conjunction with one of the studies using microphone 46 (FIG. 1), e.g. for the purpose of recording a preliminary diagnosis. The controller 12 of the present embodiment permits a digital voice recording to be made and selectively controlled (e.g. rewound or deleted) on a per-study basis, without impacting other recordings associated with other studies.

If desired, the mouse 42 may also be used to select a portion of a displayed image for magnification or other manipulation. The controller 12 provides special cursors which can be used to mark images for these or other purposes. The cursor can be moved from one display to another and may automatically change shape when different aspects of an image feature such as a tumor are being marked. For example, the cursor may automatically incorporate an "x", "y" or "z" depending upon whether the feature is being measured in the X, Y or Z dimensions, and the endpoints of a line created when making these measurements (e.g. by "dragging and dropping" the cursor) may indicate the measured dimension.

Figure 8A:
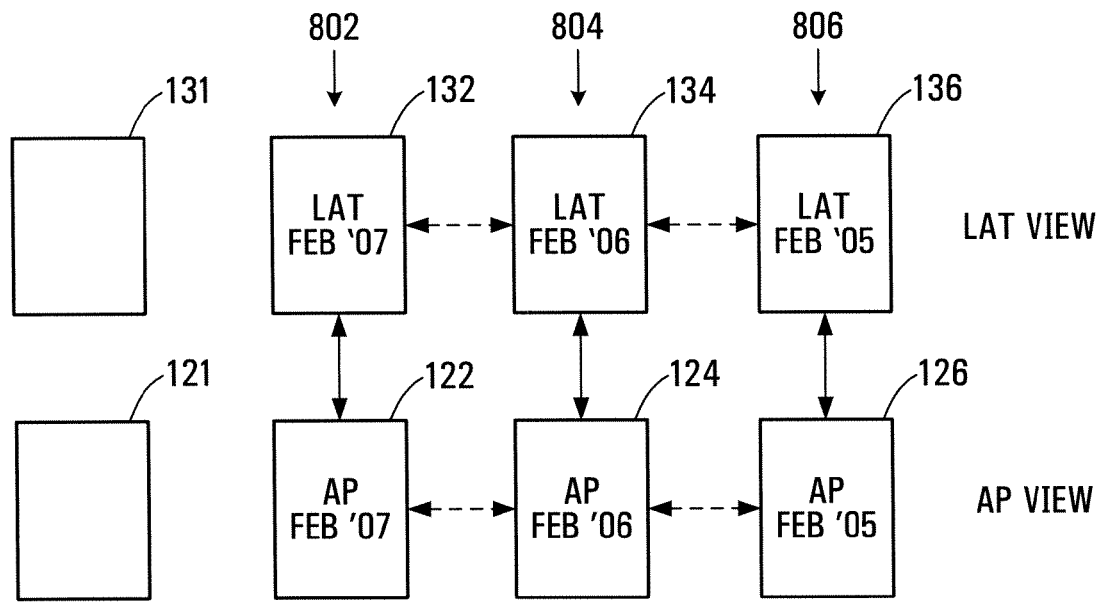
FIGS. 8A and 8B are schematic representations of displayed medical images which are displayed using an alternative approach.
Figure 8B:
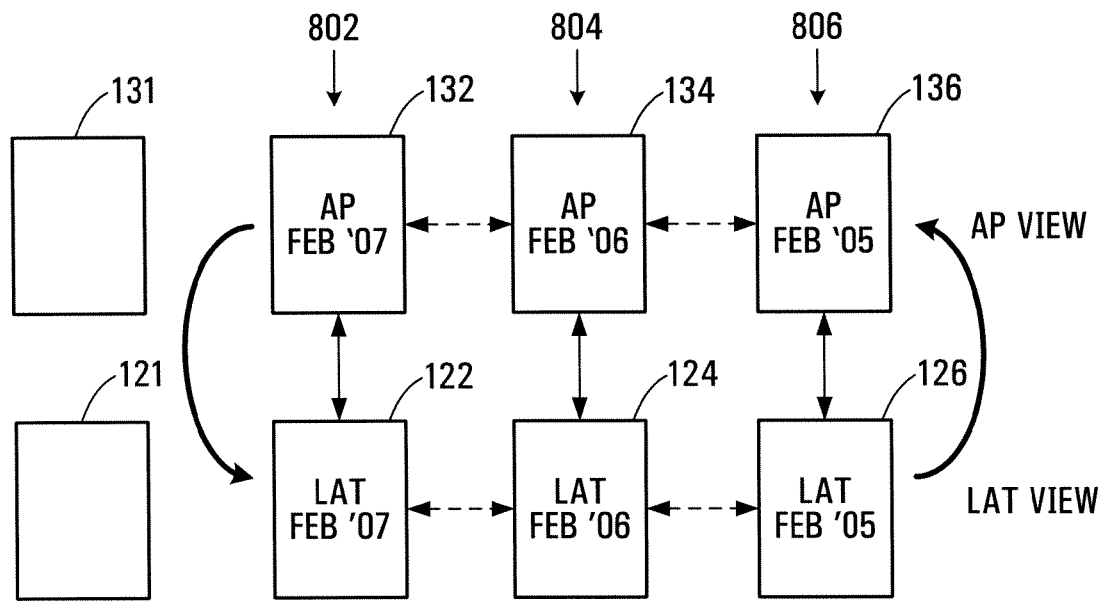

For certain types of medical image data, it may be desirable to see the images associated with a particular study arranged vertically rather than horizontally. That is, certain viewers may prefer for the linear arrays of displayed images to be vertical rather than horizontal, e.g. so that a viewer can observe the progression of a condition over time by scanning his/her eyes in a horizontal rather than vertical direction. This alternative manner of displaying images may be manually selected by the user or may be automatically selected by the system 10 based on the automatically determined nature of the studies being displayed. In the case of chest-solitary pulmonary nodule studies, for example, it may be desired for the AP view of a study to appear directly above the (substantially contemporaneous) lateral view of that study, or vice-versa. The display of image data in this fashion is illustrated in FIGS. 8A and 8B. FIGS. 8A and 8B each adopt similar conventions to FIG. 4.

The operation of the controller 12 for displaying image data is much the same as operation 300 of FIG. 3. Initially, the most recent study is identified (S302) as the "current study". For purposes of illustration, it is assumed that a February 2007 study comprising two images representing AP and lateral views of the chest is identified as the most recent study. The controller 12 may at this stage display the textual requisition data and technician report data associated with the current study on textual displays 31 and 21, resulting in content 131 and 121, respectively. Thereafter, images representing the two desired views (AP and lateral) within the study are automatically identified (S304).

The images representing the desired views are then displayed (S306). However, instead of displaying the images in a single row of graphical displays, as described above, the images are displayed in a single column of displays. More specifically, the image representing the AP view is displayed on display 22 of the first row 20 while the image representing the lateral view is displayed on display 32 of the second row 30 (FIG. 1). This results in a first linear array of medical images 802 (FIG. 8A) which is vertical. The content of displays 22, 32 is represented at 122, 132 of FIG. 8A. This assignment of images to displays constitutes an automatic ordering of the images within the array based on the represented views.

Subsequently, the next most recent study (dated February 2006) is automatically identified (S308, FIG. 3). Images representing the same views are identified within the study (S310), and the identified images are then displayed on graphical displays 24 and 34 (S312), resulting in image array 804 comprising display content 124 and 134. The images are displayed in the same order as the images displayed in the first column 802, such that like views of the patient are aligned as between the first column 802 and the second column 804 (the alignment being represented by dashed, two-headed arrows). At the same time, correlation of features between different views of the same study is also promoted (as represented in FIG. 8A by solid, two-headed arrows).

Operation S308, S310 and S312 is thereafter repeated to display medical images from a third study (dated February 2005) in a third linear array of images 806 (FIG. 8A) on displays 26 and 36, in like fashion. It is assumed that no fourth study exists, thus displays 28 and 38 may be left blank.

If the user prefers to view the lateral views in the second row of displays 30 and the AP views in the first row of displays 20, a user request to swap the views can be entered, e.g. using user input mechanism 42. The medical images displayed in the two displays of each column are then swapped by the controller 12, as shown in FIG. 8B. Entry of the command a second time reverts the images to their original positions, as shown in FIG. 8A.

When images are displayed in this fashion and the scroll wheel is rotated, and if the number of studies exceeds the number of graphical displays in a row, then a conceptual viewing window akin to window 700 (but exposing four studies at a time rather than two) may effectively be caused to slide through the chronological bundle of studies of which the displayed studies form a part, one study at a time, in the horizontal direction.

For certain types of studies, notably ultrasound or CT studies, the number of medical images I in the study may significantly exceed the number of graphical displays D. In this case, the controller 12 can automatically divide each display into cells, using a split-4, split-6, or split-9 format for example, and display the images within the cells. The choice of a format is automatic based upon the number of images I to be displayed and the number of displays D.

Referring FIG. 9A, the automatic adoption of a split-4 format is illustrated. In this example, the desired number of medical images I to be displayed is determined to be 15, and the number of displays D is 4. Using this information, the controller 12 determines that I divided by D is less than 4, meaning that a split-4 format on each of the four graphical displays would accommodate the images with room to spare. Accordingly, four images per display are displayed on each display until less than four images remain, at which point the remaining images are displayed on a single display. The result is that the first three graphical displays 22, 24 and 26 of the first array contain four images each, as shown in FIG. 5A at 122, 124 and 126, while the last display 28 contains the remaining three images, as shown at 128. One cell within the last display is left blank (hatched). It is noted that, if the number of images is twelve or less, the split-4 format could still be used, with each of the cells of the fourth display being left blank.

Turning to FIG. 9B, if the desired number of medical images I to be displayed is determined to be 16, the controller 12 determines that I divided by D is exactly 4. In this case, the split-4 format accommodates the images exactly with four images per display, as illustrated.

Referring to FIG. 9C, if the desired number of medical images I to be displayed is determined to be 17, the controller 12 determines that I divided by D is greater than 4. In this case, the split-4 format cannot accommodate all of the images. As a result, the controller 12 automatically adopts a split-6 format, as shown in FIG. 9C. Alternatively, the split-9 format could be adopted, as shown in FIG. 9D. Alternative embodiments could split displays and apportion images in other ways.

It should be appreciated that the system 10 is capable of displaying images as shown in FIGS. 9A-9D in both rows of displays 20 and 30 (FIG. 1). The system 10 can therefore effectively use its displays 18 to automatically display numerous images from multiple studies. Moreover, the same type of "scrolling" behavior that is described above in conjunction with FIG. 5 is supported when any of the split-4, split-6 or split-9 formats are used. This allows numerous additional images to be seen with minimal user input. For example, if each of the two rows of four graphical displays presents nine images per display, such that 36 images are initially displayed in each of the two rows 20 and 30, each rotation of the scroll wheel to the next detent position causes a new set of 36 images to replace one of the previously displayed sets of 36 images. Advantageously, 144 images can be viewed with only two rotations of the wheel.

As will be appreciated by those skilled in the art, modifications to the above-described embodiments can be made without departing from the essence of the invention. For example, in alternative embodiments, the number of images displayed in each linear array, and/or the number of displays per row, may be greater than that described above. Moreover, it is not absolutely required for multiple physical displays to exist. For example, the two linear arrays of images could all appear on one large display which is appropriately segmented.

In another alternative, the above-described "scrolling" operation could be triggered by something other than entry of a scrolling command by a user. For example, operation S502 of FIG. 5 could instead constitute detection of a timer countdown event, such that images are periodically scrolled automatically, or of some other type of event.

Other modifications will be apparent to those skilled in the art and, therefore, the invention is defined in the claims.

What is claimed is:

1. A computer-implemented method comprising, using at least one processor:
    displaying a first linear array of medical images representing multiple views of a patient taken approximately contemporaneously, said images being automatically ordered within the array based on the views represented in the images; and
    contemporaneously displaying a second linear array of medical images adjacent to the first linear array, the images of the second linear array representing the same views of the patient as in the first linear array and being taken approximately contemporaneously but at an earlier time from the images of the first linear array, such that like views of the patient are automatically aligned as between the first linear array and the second linear array.

2. The method of claim 1 further comprising, upon the occurrence of an event:
    replacing the medical images displayed in the first linear array with the medical images of the second linear array; and
    replacing the medical images displayed in the second linear array with a set of medical images representing the same views of said patient as in the second linear array and being taken approximately contemporaneously but at a time that is earlier than said earlier time, such that like views of the patient are aligned as between the first linear array and the second linear array.

3. The method of claim 2 wherein said event is a rotation of a scroll wheel of a user input mechanism from a first detent position to a second detent position.

4. The method of claim 1 wherein said displaying comprises presenting said first linear array of images on a first linear array of displays and wherein said contemporaneously displaying comprises contemporaneously presenting said second linear array of images on a second linear array of displays adjacent to the first linear array of displays.

5. The method of claim 4 wherein said presenting comprises, if a number of medical images I of said first array of images exceeds a number D of displays in said first array of displays, automatically presenting multiple images on at least one of the displays of the first array.

6. The method of claim 5 wherein said automatically presenting comprises reducing a size of each of said multiple images presented on said at least one of the displays.

7. The method of claim 4 wherein said presenting comprises:
    automatically displaying each medical image of said first array of images that represents a principal view of the patient on a separate one of the displays of the first array of displays; and
    further automatically displaying the remaining medical images of said first array of images on the remaining display or displays of said first array of displays.

8. The method of claim 7 wherein said further automatically displaying comprises displaying multiple images on each of said remaining display or displays of the first array.

9. The method of claim 5 wherein said automatically presenting comprises, if I divided by D is less than an integer N, displaying N images per display on one or more displays of the first array and less than N images on a remaining display or displays of the first array.

10. The method of claim 5 wherein said automatically presenting comprises, if I divided by D is greater than an integer N, automatically displaying M images per display on one or more of the displays of the first array, where M is an integer greater than N, and less than M images per display on a remaining display or displays of the first array.

11. The method of claim 10 wherein N is 4 and M is 9.

12. The method of claim 10 wherein N is 4 and M is 6.

13. The method of claim 5 wherein D is at least 3.

14. The method of claim 1 wherein said first and second linear arrays comprise rows.

15. The method of claim 1 wherein first and second linear arrays comprise columns, each column containing two displays.

16. The method of claim 15 further comprising, for each column, upon user request, swapping the medical images displayed in the two displays of column.

17. The method of claim 15 wherein said multiple views comprise a lateral view and one of a posterior-anterior view and an anterior-posterior view.

18. The method of claim 4 wherein said medical images of said first linear array comprise a set of medical images, wherein said multiple views of said patient are of a body region of said patient and further comprising:
- identifying one or more principal views of said body region of said patient in said set of medical images; and
- further identifying one or more non-principal views of said body region of said patient in said set of medical images, wherein said displaying of said first linear array of medical images comprises:
- automatically displaying each principal view in a particular size on a separate display of said first linear array of displays; and
- automatically displaying each non-principal view on the remaining display or displays of said first linear array of displays in a size that is smaller than said particular size and wherein said automatic ordering of the images within the first linear array of medical images is further based on the body region represented in said set of medical images.

19. A system for displaying medical images comprising a controller and at least one display, said controller being operable to: display on said at least one display a first linear array of medical images representing multiple views of a patient taken approximately contemporaneously, said images being automatically ordered within the array based on the views represented in the images; and contemporaneously display on said at least one display a second linear array of medical images adjacent to the first linear array, the images of the second linear array representing the same views of the patient as in the first linear array and being taken approximately contemporaneously but at an earlier time from the images of the first linear array, such that like views of the patient are automatically aligned as between the first linear array and the second linear array.

20. The system of claim 19 wherein said at least one display comprises a first linear array of displays for displaying said first linear array of medical images and a second, adjacent linear array of displays for displaying said second linear array of medical images.

21. The system of claim 20 wherein each of said first linear array of displays and second linear array of displays is a row of displays.

22. The system of claim 20 wherein each of said first linear array of displays and second linear array of displays is a column of displays.

23. A non-transitory machine-readable medium storing instructions which, when executed by a controller of a medical imaging system, cause said controller to: display a first linear array of medical images representing multiple views of a patient taken approximately contemporaneously, said images being automatically ordered within the array based on the views represented in the images; and contemporaneously display a second linear array of medical images adjacent to the first linear array, the images of the second linear array representing the same views of the patient as in the first linear array and being taken approximately contemporaneously but at an earlier time from the images of the first linear array, such that like views of the patient are automatically aligned as between the first linear array and the second linear array.

* * * * *